United States Patent [19]

Münzenmaier et al.

[11] 4,376,094
[45] Mar. 8, 1983

[54] METHOD OF DISINFECTING AND A METHOD FOR DESTROYING BACTERIA AND FUNGI USING 2-SUBSTITUTED GLUTARALDEHYDES

[75] Inventors: Wolfgang Münzenmaier, Wennigsen; Heinz Eggensperger, Hamburg; Helmut H. Ehlers, Hamburg; Wolfgang Beilfuss, Hamburg; Lothar Bücklers, Norderstedt; Hans-Peter Harke, Hamburg, all of Fed. Rep. of Germany

[73] Assignee: Sterling Drug Inc., New York, N.Y.

[21] Appl. No.: 294,892

[22] Filed: Aug. 21, 1981

[30] Foreign Application Priority Data

Aug. 30, 1980 [DE] Fed. Rep. of Germany ....... 3032795

[51] Int. Cl.³ ............................................. A61L 2/18
[52] U.S. Cl. ...................................... 422/36; 424/333
[58] Field of Search ................... 422/36; 424/333, 334, 424/304

[56] References Cited

U.S. PATENT DOCUMENTS

| | | | |
|---|---|---|---|
| 2,889,243 | 6/1959 | Underwood et al. | 422/36 |
| 3,282,775 | 11/1966 | Stonehill | 422/36 |
| 3,549,626 | 12/1970 | Miller et al. | 548/137 |
| 3,917,850 | 11/1975 | Boucher | 424/333 |
| 4,335,141 | 6/1982 | Grier et al. | 424/304 |

FOREIGN PATENT DOCUMENTS

| | | | |
|---|---|---|---|
| 1580193 | 9/1969 | France | 424/333 |
| 43-113 | 3/1968 | Japan . | |
| 564947 | 8/1975 | Switzerland | 424/333 |
| 2012263 | 7/1979 | United Kingdom | 424/333 |

OTHER PUBLICATIONS

F. Weiss et al., "Recherches sur les acetals, II.-Rearrangements thermiques de methylene-5 dioxannes-1,3 en esters methallyliques et en α-methyleneglutaraldehydes", Bull. Soc. Chim. France, 1965, 1358.
R. L. Garnick et al., "Biomimetic Transformations Among Monomeric Macroline-Related Indole Alkaloids", J. Amer. Chem. Soc., 100, 4215, 4218 (1978).
K. C. Brannock, "Preparation of 2,6-Dialkoxy-3-(-1-alkoxyalkyl)-tetrahydropyrans", J. Org. Chem. 24, 1382-1383 (1959).
R. K. Murray, Jr. et al., "On the Photochemistry of 1-Oxaspiro-[2.n]alkan-5-ones", J. Org. Chem. 42, 3994-3997 (1977).
H. A. Burch, "Dioxanes, Dithianes, and Oxathianes", Chem. Abstracts 63, P18108a (1965).
A. Losse et al., "Condensation of acetaldehyde and crotonaldehyde", Chem. Abstracts 68, 48984e (1968).
F. Camps, et al., "Formation of carbocycles in the condensation of crotonaldehyde. II. Synthesis of (E)-2-ethylidene-3-methylpentanedial (dicrotonaldehyde)", Chem. Abstracts 79, 41831w (1973).

Primary Examiner—David L. Lacey
Attorney, Agent, or Firm—Frederik W. Stonner; B. Woodrow Wyatt

[57] ABSTRACT

Disclosed is a method of disinfecting and a method for destroying bacteria and fungi employing certain 2-substituted glutaraldehydes having the formulas

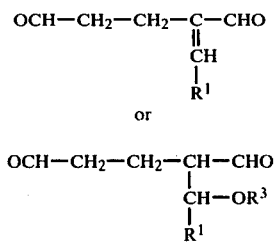

wherein $R^1$ is selected from the group consisting of alkyl having from one to twelve carbon atoms, loweralkoxyalkyl having from two to twelve carbon atoms, cycloalkyl having from three to twelve ring carbon atoms, and alkyl-substituted cycloalkyl having from three to eight ring carbon atoms and a total of from four to ten carbon atoms, and $R^3$ is alkyl having from one to four carbon atoms.

20 Claims, No Drawings

METHOD OF DISINFECTING AND A METHOD FOR DESTROYING BACTERIA AND FUNGI USING 2-SUBSTITUTED GLUTARALDEHYDES

BACKGROUND OF THE INVENTION

1. Field of the Invention

The invention relates to the use of certain 2-substituted glutaraldehydes as disinfectants.

2. Description of the Prior Art

It is known that aldehydes such as formaldehyde, glyoxal and glutaraldehyde have disinfecting action and therefore are used in disinfectants. However, there are various disadvantages in the use of these aldehydes. For example, although glyoxal is odorless and a good surface disinfectant, it is not sufficiently active in suspension tests. Other aldehydes, such as formaldehyde or glutaraldehyde, although quite active, are limited in their application and in-use concentration because of their penetrating and obnoxious odor. Furthermore, because of their volatility, their toxicologic effects must be considered.

The formation of resistant microbial strains and the process of natural selection require that new agents be found which supplement the activity of the known disinfectant agents or enhance their activity against such resistant strains. The preparation of new agents makes it possible to substitute them for presently used disinfectants and thereby decrease the formation of resistant strains.

There is a need therefore for agents which are highly active as disinfectants, are essentially odorless or have a pleasant odor, and have low volatility.

Certain 2-alkylideneglutaraldehydes are described in the art. See for example, Bull. Soc. Chim. France, 1965, 1358, J. Amer. Chem. Soc. 100, 4215, 4218 (1978), J. Org. Chem. 24, 1382-3 (1959) and 42, 3994-7 (1977), and Chem. Abstracts 63, P18108a (1965), 68, 48984e (1968) and 79, 41831w (1973). No biological utility for the 2-alkylideneglutaraldehydes is disclosed in the foregoing references.

Certain 2,6-dialkoxy-3-(1-alkoxyalkyl)tetrahydropyrans are disclosed in J. Org. Chem. 24, 1382-3 (1959). This reference discloses that the 2,6-dialkoxy-3-(1-alkoxyalkyl)tetrahydropyrans are readily converted by known methods to 2-alkylideneglutaraldehydes.

SUMMARY OF THE INVENTION

It has now been discovered that certain 2-substituted glutaraldehydes possess very good antimicrobial activity and are highly suited for use as disinfectants.

Thus, in one aspect of the invention there is provided a method for disinfecting an inanimate surface contaminated with deleterious microorganisms which comprises contacting said surface with an amount effective for disinfection thereof of a glutaraldehyde represented by the formulas

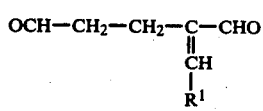

or

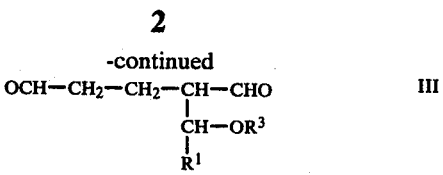

wherein $R^1$ is selected from the group consisting of alkyl having from one to twelve carbon atoms, lower-alkoxyalkyl having from two to twelve carbon atoms, cycloalkyl having from three to twelve ring carbon atoms, and alkyl-substituted cycloalkyl having from three to eight ring carbon atoms and a total of from four to ten carbon atoms, and $R^3$ is alkyl having from one to four carbon atoms.

In another aspect of the invention there is provided a method for destroying bacteria and fungi which comprises applying to them or to an environment inhabited by them a bactericidally and fungicidally effective amount of a glutaraldehyde represented by the formulas

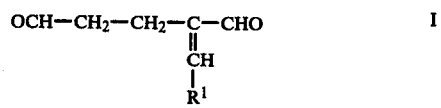

or

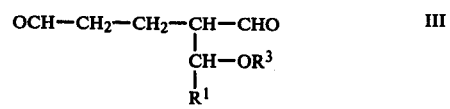

wherein $R^1$ and $R^3$ are as defined hereinabove.

The compounds of formulas I and III exhibit antibacterial and antifungal activities and are useful as antifungal and antibacterial agents, e.g., in disinfectant compositions.

DETAILED DESCRIPTION INCLUSIVE OF THE PREFERRED EMBODIMENTS

The 2-substituted glutaraldehydes of formulas I and III exhibit excellent bactericidal activity and fungicidal activity in suspension tests and are also active in surface tests (Tables 1-4 below). In contrast to the aldehydes used currently in disinfectants, the 2-substituted glutaraldehydes used in the methods of this invention, in addition to their excellent antimicrobial activity, have the advantage of being devoid of the penetrating odor associated with formaldehyde and glutaraldehyde. The higher members of this series are essentially odorless. Therefore, disinfectant compositions can be prepared with the 2-substituted glutaraldehydes in which the active aldehyde can be used in substantially higher concentrations without the disadvantage of odor problems.

"Alkyl having from one to twelve carbon atoms" as used herein refers to such a group wherein the carbon atoms can be arranged in a straight or branched chain as illustrated by methyl, ethyl, propyl, 1-methylethyl, butyl, 2-methylpropyl, 1,1-dimethylethyl, pentyl, hexyl, heptyl, octyl, nonyl, decyl and dodecyl.

"Alkyl having from one to four carbon atoms" as used herein refers to such a group which can be arranged as a straight or branched chain as illustrated by methyl, ethyl, 1-methylethyl, 1,1-dimethylethyl, propyl and butyl.

"Lower-alkoxyalkyl having from two to twelve carbon atoms" as used herein refers to such a group wherein lower-alkoxy has from one to eight carbon atoms and alkyl has from one to ten carbon atoms and wherein lower-alkoxy and alkyl each can be arranged as a straight or branched chain and the combined carbon atoms in such groups total from two to twelve as illustrated by methoxymethyl, ethoxymethyl, (1,1-dimethylhexyl)oxymethyl, 2-(ethylhexyl)oxymethyl, (1-methylheptyl)oxymethyl, 2-methoxyethyl, 2-ethoxyethyl, 1-methyl-2-methoxyethyl, 1,1-dimethyl-2-methoxyethyl, 2-(1-methylethoxy)ethyl, 2-butoxyethyl, 1,1-dimethyl-2-(1-methylethoxy)ethyl, 2-methoxypropyl, 3-ethoxypropyl, 3-heptyloxypropyl, 2-methoxybutyl, 5-butoxybutyl, 2-ethoxypentyl, 2-butoxy-1-ethylpentyl, 2-ethoxyhexyl, 5-ethoxy-1,5-dimethylhexyl, 5-methoxy-2,6-dimethylheptyl, 1-(2-methoxyethyl)heptyl, 8-ethoxyoctyl, 7-methoxy-3,7-dimethyloctyl, 8-methoxy-4,8-dimethylnonyl and 10-methoxydecyl.

As used herein, "cycloalkyl having from three to twelve ring carbon atoms" refers to an unsubstituted saturated monocyclic hydrocarbon as illustrated by cyclopropyl, cyclobutyl, cyclopentyl, cyclohexyl, cycloheptyl, cyclodecyl and cyclododecyl; and "alkyl-substituted cycloalkyl having from three to eight ring carbon atoms and a total of four to ten carbon atoms" refers to a saturated monocyclic hydrocarbon substituted by from one to four alkyl substituents which can be arranged as straight or branched chains and wherein the combined carbon atoms in cycloalkyl and the alkyl substituents total from four to ten as illustrated by 2,2-dimethylcyclopropyl, 2,3-dimethylcyclopropyl, 3-ethyl-2,2-dimethylcyclopropyl, 3-(2-methylpropyl)-2,2-dimethylcyclopropyl, 2-ethylcyclobutyl, 2-butylcyclopentyl, 1,2-dimethylcyclopentyl, 3-(1,1-dimethylethyl)cyclopentyl, 2-(1-methylethyl)cyclopentyl, 3,5-dimethylcyclohexyl, 4-(1,1-dimethylethyl)cyclohexyl, 3,3,5-trimethylcyclohexyl, 2,2,6,6-tetramethylcyclohexyl, 2,4,6-trimethylcyclohexyl, 2-methylcycloheptyl and 3-methylcyclooctyl.

The 2-substituted glutaraldehydes of formula I can be prepared by a well known procedure in which an aldehyde acetal of the formula $R^1CH=(OR^3)_2$, where $R^1$ and $R^3$ are as defined hereinabove, is condensed with a 2-($R^2O$)-2,3-dihydro-4H-pyran, where $R^2$ has the same meaning as defined hereinabove for $R^3$, in the presence of a Lewis acid such as zinc chloride or ferric chloride, followed by acid hydrolysis of the resulting corresponding 2-($R^3O$)-6-($R^2O$)-3-[1-($R^3O$)-alkyl]tetrahydropyran (II) to give the compound of formula I. The hydrolysis can be carried out with aqueous mineral acids, organic acids, or acidic emulsifying agents. Because of surprisingly excellent yields, intermediate products through which the hydrolysis proceeds need not be isolated. Solutions so obtained can, after adjustment to the desired pH, be used directly, i.e., without the need for isolating the compounds of formula I, for formulation of disinfectant compositions. In formulations prepared in this manner, there additionally can be detected 2-substituted glutaraldehydes of formula III and 2-($R^3O$)-6-($R^2O$)-3-[1-($R^3O$)-alkyl]tetrahydropyrans (II).

The partial hydrolysis product of formula III can be obtained by mild acid hydrolysis of compound II.

The antimicrobial activity of the disinfectant compositions which contain the 2-substituted glutaraldehyde of formula I on the one hand and additionally contain the partial hydrolysis products II and III on the other hand, in corresponding concentrations, are equivalent within the range of normal limits of error. Therefore, isolation of the 2-substituted glutaraldehydes in pure form by distillation is not necessary, which is of economic significance with respect to the manufacture of such compounds.

The pure 2-substituted glutaraldehydes of formula I are colorless to yellow liquids. They are insoluble in water down to the lowest members ($R^1=CH_3$, $CH_2OCH_3$), but are soluble in the usual organic solvents. These include, for example, lower alcohols such as ethanol, propan-2-ol, propan-1-ol; glycols such as ethylene glycol and triethylene glycol. On prolonged storage of the pure 2-substituted glutaraldehydes of formula I, polymerization can occur. The monomeric compounds can be regenerated in aqueous acidic solution.

The aldehyde acetal and 2-($R^2O$)-2,3-dihydro-4H-pyran starting materials each belong to known classes of compounds and can be prepared by conventional procedures.

Disinfectant compositions containing the 2-substituted glutaraldehydes of formulas I and/or III can be formulated in either acidic or basic medium. The pH of the compositions should range from about 4 to 8, preferably 5 to 7. This can be achieved by the addition of acidic agents, e.g., mineral acids such as hydrochloric and sulfuric acids; organic acids such as citric or tartaric acids; acidic emulsifying agents such as alkylsulfonic acid; or alkaline agents such as sodium hydroxide, alkali carbonates or organic amines, e.g., triethanolamine.

The disinfectant compositions can be formulated as aqueous or non-aqueous solutions employing suitable solvents as carriers. Such solvents are for example primary, secondary or tertiary mono or multifunctional aliphatic alcohols such as methanol, ethanol, propan-2-ol, propan-1-ol, ethylene glycol and glycerol.

The disinfectant compositions additionally can contain optional ingredients such as mono- or dialdehydes, e.g., formaldehyde, glyoxal or glutaraldehyde; surfactants of the class of anionic, non-ionic, cationic and amphoteric detergents; antibacterially active organic acids, such as lactic acid, citric acid, which can also be used to adjust the pH; and particular antimicrobial trisubstituted phenols, e.g., 2,6-dimethyl-4-bromophenol.

Disinfectant compositions containing the 2-substituted glutaraldehydes of formulas I and/or III have outstanding stability. On prolonged storage, no change in the physical characteristics of the compositions or loss in efficacy are discernable.

The 2-substituted glutaraldehydes of formulas I and III and disinfectant compositions containing them can be employed for the disinfection of a wide variety of inanimate surfaces contaminated with deleterious microorganisms such as are found in industrial, domestic and medical environments. For example, in a hospital environment they can be used to disinfect walls, floors and work surfaces as well as utensils such as bedpans, etc. They are particularly useful in the medical field, i.e., in human and veterinary medicine and surgery and in dentistry for disinfection of a wide variety of objects made from or containing rubber, plastic, metal and ceramics, e.g., instruments, devices and equipment such as lensed instruments, fiberoptic devices, anesthesia equipment, inhalation equipment, catheters, scalpels, scissors, forceps, needles, syringes, clamps, thermometers, etc. Such surfaces can be disinfected by contacting them with an antimicrobially effective amount of the 2-substituted glutaraldehyde using appropriate techniques well known in the art such as, for example, immersion, spraying, swabbing, etc. The amount of 2-substituted glutaraldehyde to be employed in a particular disinfectant composition and the contact time with the surface required to effect disinfection will depend on various factors such as the type of surface and the degree of contamination of the surface, and can readily be determined by one having ordinary skill in the art.

The invention is illustrated by the following examples without, however, being limited thereto.

EXAMPLE 1

(a) Procedure for preparation of 2-($R^3O$)-6-($R^2O$)-3-[1-($R^3O$)-alkyl]tetrahydropyran To 1 mole of aldehyde acetal [$R^1CH=(OR^3)_2$] is added 3 ml. of boron trifluoride etherate and then 1 mole of the 2-($R^2O$)-2,3-dihydro-4H-pyran is added dropwise with stirring. Stirring is continued one hour and the mixture is neutralized and then distilled to give the title compound. The workup can be carried out without distillation if the reaction proceeds in very good yield.

(b) Hydrolysis of 2-($R^3O$)-6-($R^2O$)-3-[1-($R^3O$)-alkyl]tetrahydropyrans

A mixture of 100 g. of the compound obtained in accordance with the procedure of Example 1a, 330 g. dioxane, 200 g. water and 40 g. concentrated hydrochloric acid is stirred for two hours at 70° C. The organic layer then is separated, neutralized and distilled to give the hydrolysis product.

By following the procedures of Examples (1a) and (1b) and using the appropriate aldehyde acetal there was obtained the following 2-substituted glutaraldehydes:

| 2-Substituted Glutaraldehyde | boiling point (°C./mm Hg) | NMR (δ) |
|---|---|---|
| 2-Ethylidene-glutaraldehyde | 72–74(4) | 2.0 d (3 H); 2.5 s (4 H); 6.7 (1 H); 9.4 s (1 H); 9.8 s (1 H) |
| 2-Butylidene-glutaraldehyde | 65–70(1) | 9.4 s (1 H); 9.8 s (1 H) |
| 2-(1-Ethoxybutyl)-glutaraldehyde | 88–92(1) | |
| 2-(2-Methylpropyli-dene)glutaraldehyde | 65–75(1) | 1.5 d (6 H); 1.7–1.8 m (1 H); 2.5 s (4 H); 6.7 d (1 H); 9.4 s (1 H); 9.8 s (1 H) |
| 2-Hexylidene-glutaraldehyde | 105–120(1) | 0.6–1.9 m (11 H); 2.5 s (4 H); 6.7 t (1 H); 9.4 s (1 H); 9.8 s (1 H) |
| 2-(Cyclohexylmethyl-ene)glutaraldehyde | 110–118(1) | 0.55–1.8 m (11 H); 2.45 s (4 H); 6.65 d (1 H); 9.5 s (1 H); 9.85 s (1 H) |
| 2-Octylidene-glutaraldehyde | 117–122(0.1) | 0.6–2.0 m (15 H); 2.45 s (4 H); 6.7 t (1 H); 9.4 s (1 H); 9.8 s (1 H) |
| 2-(2-Ethylhexyli-dene)glutaraldehyde | 146–150(10) | 0.5–1.9 m (15 H); 2.5 s (4 H); 6.65 t (1 H); 9.35 s (1 H); 9.75 s (1 H) |
| 2-(2-Methoxyethyli-dene)glutaraldehyde | 94–103(0.5) | |

EXAMPLE 2

Preparation of a 10% solution of 2-substituted glutaraldehyde of formula I without isolation of intermediates To the crude product prepared according to the procedure of Example (1a) is added 30 g. dodecylbenzenesulfonic acid (Marlon AS 3; Chemische Werke Hüls A. G., Marl, W. Germany), 50 g. triethylene glycol and 250 g. water. The mixture is heated for thirty minutes at 95° C., neutralized and 136 g. of sodium dodecylbenzenesulfonate (Phenylsulfonat HSR KONZ; Hoechst A. G., Frankfurt, W. Germany) are added. On addition of 150 g. water an approximately 10% solution of the 2-substituted glutaraldehyde is obtained.

The microbiological investigation of the individual compounds used in the methods of the invention was carried out in aqueous solution which in addition to the 2-substituted glutaraldehyde to be tested contained 5% propan-2-ol, 5% triethylene glycol and 18% sodium alkanesulfonate ($C_{10}$–$C_{18}$) (Mersolat W93; Bayer A. G., Leverkusen, W. Germany).

The microbiological tests were carried out according to the specifications for the testing of chemical disinfectants of the German Society for Hygiene and Microbiology (3rd Edition, 1972). The test results are recorded in Tables 1 to 4 below.

TABLE 1

Bactericidal Activity (Suspension Test) (killing time in minutes)

| | Concentration (Vol. %) (active ingredient) | Staphylococcus aureus | Klebsiella pneumoniae | Pseudomonas aeruginosa | Proteus vulgaris |
|---|---|---|---|---|---|
| 2-Ethylidene-glutaraldehyde | 0.1 | 2.5 | 2.5 | 2.5 | 2.5 |
| | 0.05 | 2.5 | 2.5 | 5 | 5 |
| | 0.025 | 5 | 5 | 15 | 15 |
| | 0.01 | 15 | 15 | >30 | 15 |
| | 0.005 | 30 | 30 | | 30 |
| 2-Butylidene-glutaraldehyde | 0.02 | 2.5 | 2.5 | 2.5 | 2.5 |
| | 0.01 | 2.5 | 2.5 | 2.5 | 2.5 |
| | 0.005 | 5 | 2.5 | >30 | 2.5 |
| | 0.0025 | 15 | 5 | | 5 |
| | 0.001 | 30 | 30 | | 15 |
| 2-(1-Ethoxybutyl)-glutaraldehyde | 0.025 | 5 | 2.5 | >30 | 2.5 |
| | 0.01 | 15 | 5 | | 5 |
| | 0.005 | 15 | 15 | | 15 |
| | 0.0025 | 30 | >30 | | 30 |
| | 0.001 | >30 | | | 30 |
| 2-(2-Methylpropyli-dene)glutaraldehyde | 0.025 | 5 | 2.5 | 2.5 | 2.5 |
| | 0.01 | 15 | 5 | 30 | 5 |
| | 0.005 | 15 | 15 | >30 | 15 |

TABLE 1-continued

Bactericidal Activity (Suspension Test) (killing time in minutes)

| | Concentration (Vol. %) (active ingredient) | Staphylococcus aureus | Klebsiella pneumoniae | Pseudomonas aeruginosa | Proteus vulgaris |
|---|---|---|---|---|---|
| | 0.0025 | 30 | 15 | | 15 |
| | 0.001 | >30 | >30 | | 30 |
| 2-Hexylidene-glutaraldehyde | 0.025 | 2.5 | 5 | >30 | 2.5 |
| | 0.01 | 2.5 | >30 | | 30 |
| | 0.005 | 15 | | | 30 |
| 2-(Cyclohexylmethylene)glutaraldehyde | 0.025 | 2.5 | 5 | 5 | 2.5 |
| | 0.01 | 2.5 | 5 | 15 | 2.5 |
| | 0.005 | 5 | 15 | >30 | 5 |
| | 0.0025 | 15 | 30 | | 15 |
| | 0.001 | 30 | >30 | | 30 |
| | 0.0005 | >30 | | | >30 |
| 2-Octylidene-glutaraldehyde | 0.025 | 2.5 | 30 | >30 | 5 |
| | 0.01 | 2.5 | 30 | | 5 |
| | 0.005 | 2.5 | >30 | | 5 |
| | 0.001 | 5 | | | >30 |
| | 0.0001 | 30 | | | |
| 2-(2-Ethylhexylidene)glutaraldehyde | 0.25 | 2.5 | 30 | 15 | 2.5 |
| | 0.1 | 5 | 30 | 30 | 2.5 |
| | 0.05 | 5 | >30 | >30 | 5 |
| Glutaraldehyde | 0.2 | 2.5 | 5 | 5 | 15 |
| | 0.1 | 5 | 15 | 15 | 30 |
| | 0.05 | 15 | 15 | 30 | 30 |
| | 0.025 | >30 | >30 | >30 | >30 |

TABLE 2

Bactericidal Activity With A 20% Serum Load (Suspension Test) (killing time in minutes)

| | Concentration (Vol. %) (active ingredient) | Staphylococcus aureus | Klebsiella pneumoniae | Pseudomonas aeruginosa | Proteus vulgaris |
|---|---|---|---|---|---|
| 2-Ethylidene-glutaraldehyde | 0.1 | 2.5 | 2.5 | 2.5 | 2.5 |
| | 0.05 | 15 | 5 | 30 | 5 |
| | 0.025 | 15 | >30 | >30 | 15 |
| 2-Butylidene-glutaraldehyde | 0.025 | 2.5 | 2.5 | 15 | 2.5 |
| | 0.01 | 5 | 5 | >30 | 2.5 |
| | 0.005 | 30 | >30 | | 5 |
| Glutaraldehyde | 0.2 | 2.5 | 2.5 | 5 | 2.5 |
| | 0.1 | 5 | 5 | >30 | 30 |
| | 0.05 | >30 | 30 | | 30 |

TABLE 3

Fungicidal Activity (Suspension Test) (killing time in minutes)

| | Concentration (Vol. %) (active ingredient) | Trichophyton mentagrophytes | Candida albicans | Aspergillus niger |
|---|---|---|---|---|
| 2-Ethylidene-glutaraldehyde | 0.05 | 15 | 2.5 | 15 |
| | 0.025 | >30 | 15 | 30 |
| | 0.01 | | >30 | >30 |
| 2-Butylidene-glutaraldehyde | 0.02 | 2.5 | 2.5 | 2.5 |
| | 0.01 | 2.5 | 2.5 | 2.5 |
| | 0.005 | 2.5 | 2.5 | 15 |
| | 0.0025 | 5 | 2.5 | >30 |
| | 0.001 | 5 | 15 | |
| 2-(1-Ethoxybutyl)-glutaraldehyde | 0.01 | 2.5 | 2.5 | >30 |
| | 0.005 | 5 | 5 | |
| | 0.0025 | 15 | >30 | |
| | 0.001 | 30 | | |
| 2-(3-Methylbutylidene)glutaraldehyde | 0.025 | 2.5 | 2.5 | 2.5 |
| | 0.01 | 2.5 | 2.5 | 5 |
| | 0.005 | 2.5 | 2.5 | 30 |
| | 0.0025 | 5 | 2.5 | >30 |
| | 0.001 | 15 | 30 | |
| 2-Hexylidene-glutaraldehyde | 0.025 | 2.5 | 2.5 | 15 |
| | 0.01 | 2.5 | 2.5 | 30 |
| | 0.005 | 2.5 | 2.5 | >30 |
| 2-(Cyclohexylmethylene)glutaraldehyde | 0.01 | 2.5 | 2.5 | >30 |
| | 0.005 | 2.5 | 2.5 | |
| | 0.0025 | 2.5 | 2.5 | |
| | 0.001 | 2.5 | 2.5 | |
| | 0.0005 | 2.5 | 30 | |
| 2-Octylidene-glutaraldehyde | 0.01 | 2.5 | 2.5 | 15 |
| | 0.005 | 2.5 | 2.5 | 30 |
| | 0.0025 | 2.5 | 2.5 | >30 |
| | 0.001 | 2.5 | 2.5 | |

TABLE 3-continued

| | Fungicidal Activity (Suspension Test) (killing time in minutes) | | | |
|---|---|---|---|---|
| | Concentration (Vol. %) (active ingredient) | *Trichophyton mentagrophytes* | *Candida albicans* | *Aspergillus niger* |
| | 0.0005 | 2.5 | 5 | |
| | 0.00025 | 15 | 15 | |
| | 0.0001 | >30 | >30 | |
| 2-(2-Ethylhexyli- | 0.25 | >30 | >30 | 30 |
| dene)glutaraldehyde | 0.1 | | | >30 |
| Glutaraldehyde | 0.2 | 2.5 | 30 | >30 |
| | 0.1 | 2.5 | 30 | |
| | 0.05 | 5 | >30 | |
| | 0.03 | 15 | | |
| | 0.01 | 30 | | |

TABLE 4

| | Surface Activity (killing time in hours) | | | |
|---|---|---|---|---|
| | Concentration (Vol. %) (active ingredient) | *Staphylococcus aureus* | | *Escherichia coli* | |
| | | PVC | Wood Lacquer | PVC | Wood Lacquer |
| 2-Ethylidene- | 0.1 | 1 | 1 | 1 | 1 |
| glutaraldehyde | 0.05 | >6 | >6 | 1 | 1 |
| | 0.025 | | | 4 | 1 |
| 2-(3-Methyl- | 0.02 | 1 | 1 | | |
| butylidene) | 0.01 | >6 | 1 | | |
| glutaraldehyde | 0.005 | | >6 | | |
| 2-(Cyclohexyl- | 0.04 | 1 | 1 | | |
| methylene) | 0.02 | 2 | 1 | | |
| glutaraldehyde | 0.01 | >6 | 6 | | |
| | 0.005 | | >6 | | |
| Glutaraldehyde | 0.2 | 1 | 1 | 1 | 1 |
| | 0.1 | 6 | 6 | 4 | 4 |
| | 0.05 | | | 6 | 6 |
| Glyoxal | 0.1 | 1 | 1 | 1 | 1 |
| | 0.05 | 2 | 2 | 2 | 1 |
| | 0.01 | 6 | 6 | 6 | 6 |

We claim:

1. A method for disinfecting an inanimate surface contaminated with deleterious microorganisms which comprises contacting said surface with an amount effective for disinfection thereof of a glutaraldehyde represented by the formulas

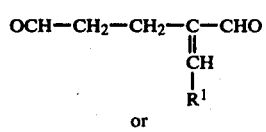

or

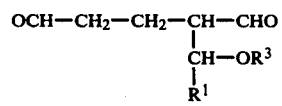

wherein $R^1$ is selected from the group consisting of alkyl having from one to twelve carbon atoms, lower-alkoxyalkyl having from two to twelve carbon atoms, cycloalkyl having from three to twelve ring carbon atoms, and alkyl-substituted cycloalkyl having from three to eight ring carbon atoms and a total of from four to ten carbon atoms, and $R^3$ is alkyl having from one to four carbon atoms.

2. A method according to claim 1 wherein $R^1$ is selected from the group consisting of alkyl having from one to eight carbon atoms, lower-alkoxyalkyl having from two to four carbon atoms, cycloalkyl having from three to seven ring carbon atoms and alkyl-substituted cycloalkyl having from three to seven ring carbon atoms and a total of from four to ten carbon atoms.

3. A method according to claim 2 wherein said cycloalkyl is cyclohexyl or alkyl-substituted cyclohexyl having a total of from seven to ten carbon atoms.

4. A method according to claim 3 wherein $R^3$ is methyl or ethyl.

5. A method according to claim 4 wherein the glutaraldehyde is 2-(1-ethoxybutyl)glutaraldehyde.

6. A method according to claim 3 wherein the glutaraldehyde is represented by the formula

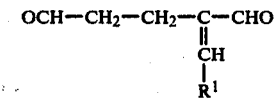

7. A method according to claim 6 wherein the glutaraldehyde is selected from the group consisting of 2-ethylideneglutaraldehyde, 2-butylideneglutaraldehyde, 2-(2-methylpropylidene)glutaraldehyde, 2-hexylideneglutaraldehyde, 2-(2-ethylhexylidene)glutaraldehyde, 2-octylideneglutaraldehyde and 2-(cyclohexylmethylene)glutaraldehyde.

8. A method according to claim 6 wherein the glutaraldehyde is 2-(2-methoxyethylidene)glutaraldehyde.

9. A method according to claim 2 wherein the glutaraldehyde is represented by the formula

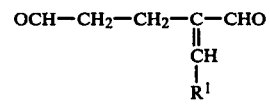

10. A method according to claim 1 wherein the glutaraldehyde is represented by the formula

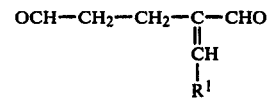

11. A method for destroying bacteria and fungi which comprises applying to them or to an environment inhabited by them a bactericidally and fungicidally effective amount of a glutaraldehyde represented by the formulas

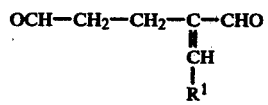

or

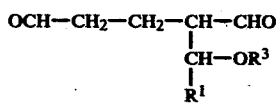

wherein $R^1$ is selected from the froup consisting of alkyl having from one to twelve carbon atoms, lower-alkoxyalkyl having from two to twelve carbon atoms, cycloalkyl having from three to twelve ring carbon atoms, and alkyl-substituted cycloalkyl having from three to eight ring carbon atoms and a total of from four to ten carbon atoms, and $R^3$ is alkyl having from one to four carbon atoms.

12. A method according to claim 11 wherein $R^1$ is selected from the group consisting of alkyl having from one to eight carbon atoms, lower-alkoxyalkyl having from two to four carbon atoms, cycloalkyl having from three to seven ring carbon atoms and alkyl-substituted cycloalkyl having from three to seven ring carbon atoms and a total of from four to ten carbon atoms.

13. A method according to claim 12 wherein said cycloalkyl is cyclohexyl or alkyl-substituted cyclohexyl having a total of from seven to ten carbon atoms.

14. A method according to claim 13 wherein the glutaraldehyde is represented by the formula

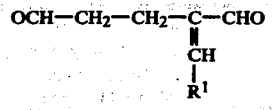

15. A method according to claim 14 wherein the glutaraldehyde is selected from the group consisting of 2-ethylideneglutaraldehyde, 2-butylideneglutaraldehyde, 2-(2-methylpropylidene)glutaraldehyde, 2-hexylideneglutaraldehyde, 2-(2-ethylhexylidene)glutaraldehyde, 2-octylideneglutaraldehyde and 2-(cyclohexylmethylene)glutaraldehyde.

16. A method according to claim 14 wherein the glutaraldehyde is 2-(2-methoxyethylidene)glutaraldehyde.

17. A method according to claim 12 wherein the glutaraldehyde is represented by the formula

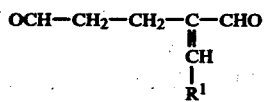

18. A method according to claim 13 wherein $R^3$ is methyl or ethyl.

19. A method according to claim 18 wherein the glutaraldehyde is 2-(1-ethoxybutyl)glutaraldehyde.

20. A method according to claim 11 wherein the glutaraldehyde is represented by the formula

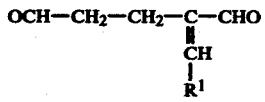

* * * * *